United States Patent
Jamison et al.

(10) Patent No.: US 9,664,036 B2
(45) Date of Patent: May 30, 2017

(54) SYSTEMS AND METHODS FOR MEASURING DOWNHOLE FLUID CHARACTERISTICS IN DRILLING FLUIDS

(71) Applicant: Halliburton Energy Services, Inc., Houston, TX (US)

(72) Inventors: Dale E. Jamison, Humble, TX (US); Cato Russell McDaniel, Montgomery, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 393 days.

(21) Appl. No.: 14/377,422

(22) PCT Filed: Oct. 9, 2013

(86) PCT No.: PCT/US2013/063980
§ 371 (c)(1),
(2) Date: Aug. 7, 2014

(87) PCT Pub. No.: WO2015/053759
PCT Pub. Date: Apr. 16, 2015

(65) Prior Publication Data
US 2015/0330215 A1    Nov. 19, 2015

(51) Int. Cl.
*E21B 47/10* (2012.01)
*G01N 11/00* (2006.01)
(Continued)

(52) U.S. Cl.
CPC ............ *E21B 47/102* (2013.01); *G01N 11/00* (2013.01); *G01N 15/0205* (2013.01);
(Continued)

(58) Field of Classification Search
CPC ....................................................... E21B 47/10
(Continued)

(56) References Cited

U.S. PATENT DOCUMENTS

| 4,994,671 A | * | 2/1991 | Safinya | E21B 47/102 250/253 |
| 5,166,747 A | * | 11/1992 | Schroeder | E21B 47/102 250/256 |

(Continued)

FOREIGN PATENT DOCUMENTS

| EP | 0435570 A1 | 7/1991 |
| WO | 2008121715 A1 | 10/2008 |
| WO | 2015053759 A1 | 4/2015 |

OTHER PUBLICATIONS

International Search Report and Written Opinion for PCT/US2013/063980 dated Jul. 3, 2014.*

*Primary Examiner* — Clayton E Laballe
*Assistant Examiner* — Kevin Butler
(74) *Attorney, Agent, or Firm* — McDermott Will & Emery LLP (57) ABSTRACT

Disclosed are systems and methods for monitoring drilling fluids. One system includes a flow path containing a fluid having at least one component present therein, and a movable housing having at least one optical computing device configured to move with the movable housing along a detection path, the at least one optical computing device including at least one integrated computational element (ICE) configured to optically interact with the fluid over the detection path, wherein the at least one ICE is configured to detect a characteristic of the at least one component and generate an output signal corresponding to the characteristic.

19 Claims, 4 Drawing Sheets

(51) Int. Cl.
  *G01N 15/02* (2006.01)
  *G01N 21/03* (2006.01)
  *G01N 21/27* (2006.01)
  *G01N 21/3577* (2014.01)
  *G01N 21/85* (2006.01)
  *E21B 21/08* (2006.01)
  *E21B 49/00* (2006.01)
  *G01N 33/28* (2006.01)
  *G01N 21/05* (2006.01)

(52) U.S. Cl.
  CPC ....... *G01N 21/0303* (2013.01); *G01N 21/274* (2013.01); *G01N 21/3577* (2013.01); *G01N 21/85* (2013.01); *E21B 21/08* (2013.01); *E21B 47/10* (2013.01); *E21B 49/005* (2013.01); *G01N 21/05* (2013.01); *G01N 33/2823* (2013.01); *G01N 2021/0375* (2013.01); *G01N 2021/0389* (2013.01); *G01N 2021/0396* (2013.01); *G01N 2021/8557* (2013.01); *G01N 2021/8592* (2013.01); *G01N 2201/129* (2013.01)

(58) Field of Classification Search
  USPC ..................................................... 73/152.42
  See application file for complete search history.

(56) References Cited

U.S. PATENT DOCUMENTS

| | | | | |
|---|---|---|---|---|
| 6,176,323 B1* | 1/2001 | Weirich | .................. | E21B 21/08 175/40 |
| 6,274,865 B1* | 8/2001 | Schroer | ................ | E21B 47/102 250/255 |
| 6,350,986 B1* | 2/2002 | Mullins | ................ | E21B 47/102 250/255 |
| 7,036,362 B2* | 5/2006 | Haddad | ................ | E21B 49/08 73/152.05 |
| 7,236,237 B2* | 6/2007 | Schmilovitch | ......... | G01N 21/05 119/14.14 |
| 7,614,294 B2* | 11/2009 | Hegeman | .............. | E21B 49/081 73/152.39 |
| 7,782,460 B2* | 8/2010 | DiFoggio | ................ | G01N 21/31 250/263 |
| 8,427,640 B2 | 4/2013 | Ronaes et al. | | |
| 8,812,236 B1* | 8/2014 | Freeman | ................ | E21B 21/065 175/66 |
| 8,955,376 B2* | 2/2015 | Pelletier | .................. | E21B 49/10 73/152.42 |
| 9,234,835 B2* | 1/2016 | Pelletier | ............ | G01N 21/1702 |
| 2003/0084717 A1* | 5/2003 | Herzhaft | ................ | G01N 11/16 73/152.19 |
| 2006/0139646 A1* | 6/2006 | DiFoggio | ................ | E21B 49/10 356/436 |
| 2006/0142955 A1* | 6/2006 | Jones | .................... | E21B 47/102 702/32 |
| 2009/0049904 A1* | 2/2009 | Meister | ................... | E21B 49/10 73/152.23 |
| 2009/0087911 A1* | 4/2009 | Ramos | ................ | E21B 47/1015 436/27 |
| 2009/0126928 A1* | 5/2009 | Sumrall | ............. | G01N 33/2823 166/250.01 |
| 2009/0294175 A1* | 12/2009 | Cartellieri | ................ | E21B 47/10 175/50 |
| 2010/0265509 A1* | 10/2010 | Jones | .................... | E21B 47/102 356/445 |
| 2011/0000294 A1* | 1/2011 | Kimour | .............. | B01D 53/0423 73/152.04 |
| 2011/0016962 A1* | 1/2011 | DiFoggio | ................ | E21B 49/10 73/152.15 |
| 2012/0043966 A1* | 2/2012 | Montaron | .............. | G01V 5/104 324/324 |
| 2012/0150451 A1* | 6/2012 | Skinner | .............. | G01N 33/2823 702/24 |
| 2013/0032345 A1* | 2/2013 | Freese | ...................... | C09K 8/72 166/279 |
| 2013/0034842 A1* | 2/2013 | Tunheim | .............. | G01N 21/85 435/3 |
| 2013/0056626 A1* | 3/2013 | Shen | ........................ | E21B 47/10 250/269.1 |
| 2013/0062514 A1* | 3/2013 | Csutak | .................. | G01J 3/0256 250/262 |
| 2013/0068940 A1* | 3/2013 | Jones | .................... | E21B 47/102 250/253 |
| 2013/0104642 A1* | 5/2013 | Pelletier | .................. | E21B 49/10 73/152.47 |
| 2013/0334412 A1* | 12/2013 | Gunn | ................. | G01N 33/2823 250/255 |
| 2014/0076551 A1* | 3/2014 | Pelletier | .................. | G01N 21/47 166/253.1 |
| 2014/0166871 A1* | 6/2014 | Jamison | .................. | E21B 49/08 250/254 |
| 2014/0208826 A1* | 7/2014 | Larter | ..................... | E21B 49/06 73/23.41 |
| 2015/0260703 A1* | 9/2015 | Mitchell | .................. | E21B 47/00 73/19.09 |
| 2015/0322772 A1* | 11/2015 | Pelletier | ................... | E21B 47/01 250/254 |
| 2015/0330215 A1* | 11/2015 | Jamison | ................ | E21B 47/102 73/152.42 |
| 2016/0102510 A1* | 4/2016 | Mitchell | ................ | E21B 47/102 175/24 |
| 2016/0290131 A1* | 10/2016 | Mitchell | ................ | E21B 47/102 |

* cited by examiner

SYSTEMS AND METHODS FOR MEASURING DOWNHOLE FLUID CHARACTERISTICS IN DRILLING FLUIDS

BACKGROUND

The present disclosure relates to systems and methods for monitoring drilling fluids and, more specifically, for determining quantities, distributions, and other characteristics of interest of components within a drilling fluid using optical computing devices.

During the drilling of a hydrocarbon-producing well, a drilling fluid or "mud" is continuously circulated from the surface down to the bottom of the wellbore being drilled and back to the surface again. Prior to being conveyed downhole, the fluid may be treated by adding or removing components to obtain a predetermined mixture designed for optimal efficiency of the fluid. However, due to natural tendencies, the fluid mixture may change during circulation. For example, one problem is the loss of certain sized drilling fluid components through pores of the wellbore wall. Such loss will result in a different particle size distribution (PSD) of drilling fluid components. To counteract this, a well operator may add lost circulation materials (LCM), such as ground peanut shells, mica, cellophane, calcium carbonate, etc., to the fluid to form a filter cake on the wellbore wall and reduce or prevent further fluid loss. Some portions of various LCM compositions, however, may be removed from the drilling fluid due to intended consumption or through the use of shaker screens or other solids control units. Another issue that may arise, also affecting component PSD, is particle size attrition due to particles breaking down or otherwise being ground to smaller sizes while circulating through the drill pipe, out the drill bit, and within the wellbore.

Currently, tests to measure PSD of drilling fluid may be performed on a sample of the drilling fluid taken out of the flow line. As this fails to give real-time feedback to the operator, methods such as laser diffraction may be used to sample the drilling fluid at a predetermined point in the flow line. While these current methods and techniques return information pertaining to particle sizes within the drilling fluid, one of skill in the art will appreciate that additional information regarding particle type and particle morphology may allow further refinement and efficiency of the drilling fluid.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to systems and methods for monitoring drilling fluids and, more specifically, for determining quantities, distributions, and other characteristics of interest of components within a drilling fluid using optical computing devices.

The exemplary systems and methods described herein employ various configurations of optical computing devices, also commonly referred to as "opticoanalytical devices," for the real-time or near real-time monitoring of a fluid, such as a drilling fluid or a completion fluid. In operation, the exemplary systems and methods may be useful and otherwise advantageous in determining one or more properties or characteristics of the fluid, such as a concentration of one or more components or substances present within the fluid. The optical computing devices, which are described in more detail below, can advantageously provide real-time fluid monitoring that cannot presently be achieved with either onsite analyses at a job site or via more detailed analyses that take place in a laboratory. A significant and distinct advantage of these devices is that they can be configured to specifically detect and/or measure a particular component or characteristic of interest of a fluid, thereby allowing qualitative and/or quantitative analyses of the fluid to occur without having to extract a sample and undertake time-consuming analyses of the sample at an off-site laboratory. With the ability to undertake real-time or near real-time analyses, the exemplary systems and methods described herein may be able to provide some measure of proactive or responsive control over the fluid flow, thereby optimizing related operations.

The systems and methods disclosed herein may be suitable for use in the oil and gas industry since the described optical computing devices provide a cost-effective, rugged, and accurate means for monitoring oil/gas-related fluids, such as drilling fluids or completion fluids, in order to facilitate the efficient management of wellbore operations. Those skilled in the art, however, will readily recognize that the presently disclosed systems and methods may equally be advantageous and otherwise applicable to other fields of technology or industry including, but not limited to, the food industry, the paint industry, the mining industry, the agricultural industry, the medical industry and pharmaceutical industry, the automotive industry, the cosmetics industry, the water treatment industry, and any other industry where it may be desired to determine the size and particle size distribution of components of a fluid. The optical computing devices (or an array thereof) can be deployed various points within a flow path to monitor the fluid and the various parameter changes that may occur thereto. Depending on the location of the particular optical computing device, different types of information about the fluid can be obtained.

In some cases, for example, the optical computing devices can be used to monitor changes to the fluid following circulation of the fluid into and out of a wellbore. Drilling fluid parameters being monitored may include measurement of particle size and morphology (e.g., shape). Furthermore, calculations may be performed to determine overall particle size distribution (PSD) or loss of lost circulation material (LCM). In other embodiments, the optical computing devices can be used to monitor the fluid as a result of adding a component or substance thereto, or otherwise removing a component or substance therefrom. Thus, the systems and methods described herein may be configured to monitor a flow of fluids and, more particularly, to monitor the present state of the fluid and any changes thereto with respect to any constituent components present therein.

As used herein, the term "fluid" refers to any substance that is capable of flowing, including particulate solids, liquids, gases, slurries, emulsions, powders, muds, mixtures, combinations thereof, and the like. In some embodiments, the fluid may be a drilling fluid or drilling mud, including water-based drilling fluids, oil-based drilling fluids, synthetic drilling fluids, and the like. In other embodiments, the fluid may be a completion fluid or clean-up fluid such as, but not limited to, fresh water, saltwater (e.g., water containing one or more salts dissolved therein), brine (e.g., saturated salt water, chloride salts, bromide salts, combinations thereof, etc.), seawater, a spacer fluid, base fluids, or other treatment fluids known in the art.

As used herein, the term "characteristic" refers to a chemical, mechanical, or physical property of a substance, such as a fluid, or a component within the fluid. A characteristic of a substance may include a quantitative value of one or more chemical constituents therein or physical properties associated therewith. Such chemical constituents may be referred to herein as "analytes." Illustrative characteristics of a substance that can be monitored with the optical computing devices disclosed herein can include, for example, chemical composition (e.g., identity and concentration in total or of individual components), phase presence (e.g., gas, oil, water, etc.), impurity content, pH, alkalinity, viscosity, density, particle size, particle size distribution, morphology, shape, chord length of particles, ionic strength, total dissolved solids, salt content (e.g., salinity), porosity, opacity, bacteria content, total hardness, combinations thereof, state of matter (solid, liquid, gas, emulsion, mixtures, etc), and the like. Moreover, the phrase "characteristic of interest of/in a fluid" may be used herein to refer to the characteristic of a substance contained in or otherwise flowing with the fluid.

As used herein, the term "flow path" refers to a route through which a fluid is capable of being transported between at least two points. In some cases, the flow path need not be continuous or otherwise contiguous between the two points. Exemplary flow paths include, but are not limited to, a flow line, a pipeline, production tubing, drill string, work string, casing, a wellbore, an annulus defined between a wellbore and any tubular arranged within the wellbore, a mud pit, a subterranean formation, etc., combinations thereof, or the like. It should be noted that the term "flow path" does not necessarily imply that a fluid is flowing therein, rather that a fluid is capable of being transported or otherwise flowable therethrough.

As used herein, the term "component," or variations thereof, refers to at least a portion of a substance or material of interest in the fluid to be evaluated using the optical computing devices described herein. In some embodiments, the component is the characteristic of interest, as defined above, and may include any integral constituent of the fluid flowing within the flow path. For example, the component may include compounds containing elements such as barium, calcium (e.g., calcium carbonate), carbon (e.g., graphitic resilient carbon), chlorine (e.g., chlorides), manganese, sulfur, iron, strontium, chlorine, etc., and any chemical substance that may lead to precipitation within a flow path. The component may also refer to paraffins, waxes, asphaltenes, clays (e.g., smectite, illite, kaolins, etc.), aromatics, saturates, foams, salts, particulates, hydrates, sand or other solid particles (e.g., low and high gravity solids), combinations thereof, and the like. In yet other embodiments, in terms of quantifying ionic strength, the component may include various ions, such as, but not limited to, $Ba_2^+$, $Sr_2^+$, $Fe^+$, $Fe_2^+$ (or total Fe), $Mn_2^+$, $SO_4^{2-}$, $CO_3^{2-}$, $Ca_2^+$, $Mg_2^+$, $Na^+$, $K^+$, $Cl^-$.

In other aspects, the component may refer to any substance or material added to the fluid as an additive or in order to treat the fluid or the flow path. For instance, the component may include, but is not limited to, acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents and emulsifiers, de-emulsifying agents, iron control agents, proppants or other particulates, gravel, particulate diverters, salts, fluid loss control additives, gases, catalysts, clay control agents, clay stabilizers, clay inhibitors, chelating agents, corrosion inhibitors, dispersants, flocculants, base fluids (e.g., water, brines, oils), scavengers (e.g., $H_2S$ scavengers, $CO_2$ scavengers or $O_2$ scavengers), lubricants, breakers, delayed release breakers, friction reducers, bridging agents, viscosifiers, thinners, high-heat polymers, tar treatments, weighting agents or materials (e.g., barite, etc.), solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, and the like. Combinations of these substances can be referred to as a substance as well.

The component may further refer to LCM added to or removed from the fluid. In some embodiments, LCM may comprise particulate, fibers, or both. Examples of suitable LCM may include, but are not limited to, sand, shale, ground marble, bauxite, ceramic materials, glass materials, metal pellets, high strength synthetic fibers, resilient graphitic carbon, cellulose flakes, wood, resins, polymer materials (crosslinked or otherwise), polytetrafluoroethylene materials, nut shell pieces, cured resinous particulates comprising nut shell pieces, seed shell pieces, cured resinous particulates comprising seed shell pieces, fruit pit pieces, cured resinous particulates comprising fruit pit pieces, composite materials, and any combination thereof. Suitable composite materials may comprise a binder and a filler material wherein suitable filler materials include silica, alumina, fumed carbon, carbon black, graphite, mica, titanium dioxide, meta-silicate, calcium silicate, kaolin, talc, zirconia, boron, fly ash, hollow glass microspheres, solid glass, and any combination thereof.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation associated with a fluid and produce an output of electromagnetic radiation from a processing element arranged within the optical computing device. The processing element may be, for example, an integrated computational element (ICE), also known as a multivariate optical element (MOE), used in the optical computing device. The electromagnetic radiation that optically interacts with the processing element is changed so as to be readable by a detector, such that an output of the detector can be correlated to a characteristic of the fluid or a component present within the fluid. The output of electromagnetic radiation from the processing element can be reflected electromagnetic radiation, transmitted electromagnetic radiation, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements or multivariate optical elements), a fluid, or a component present within the fluid. Accordingly, optically interacted light refers to electromagnetic radiation that has been reflected, transmitted, scattered, diffracted, or absorbed by, emitted, or re-radiated, for example, using a processing element, but may also apply to interaction with a fluid or a component of the fluid.

The exemplary systems and methods described herein will include at least one optical computing device arranged along or in a flow path in order to monitor a fluid contained therein. Each optical computing device may include an electromagnetic radiation source, at least one processing element (e.g., an integrated computational element), and at least one detector arranged to receive optically interacted light from the at least one processing element or the fluid. In some embodiments, the exemplary optical computing devices may be specifically configured for detecting, analyzing, and quantitatively measuring a particular characteristic of the fluid or a component present within the fluid. In other embodiments, the optical computing devices may be general purpose optical devices, with post-acquisition processing (e.g., through computer means) being used to specifically detect the characteristic of the sample.

The presently described optical computing devices can perform calculations (analyses) in real-time or near real-time without the need for time-consuming sample processing. Moreover, the optical computing devices can be specifically configured to detect and analyze particular characteristics of a fluid or a component present within the fluid. As a result, interfering signals are discriminated from those of interest in the fluid by appropriate configuration of the optical computing devices, such that the optical computing devices provide a rapid response regarding the characteristics of the fluid as based on the detected output. In some embodiments, the detected output can be converted into a voltage that is distinctive of the magnitude of the characteristic of the fluid or a component present therein.

The optical computing devices can be configured to detect not only the composition and concentrations of a fluid or a component therein, but they also can be configured to determine physical properties and other characteristics of the fluid and/or component as well, based on an analysis of the electromagnetic radiation received from the fluid and/or component. For example, the optical computing devices can be configured to determine the concentration of an analyte and correlate the determined concentration to a characteristic of the fluid or component by using suitable processing means. In other embodiments, the optical computing devices may be configured to measure the real-time particle size distribution of a fluid. As will be appreciated, the optical computing devices may be configured to detect as many characteristics of the fluid or component as desired. All that is required to accomplish the monitoring of multiple characteristics is the incorporation of suitable processing and detection means within the optical computing device for each characteristic. In some embodiments, the properties of the fluid or component can be a combination of the properties of the analytes therein (e.g., a linear, non-linear, logarithmic, and/or exponential combination). Accordingly, the more characteristics and analytes that are detected and analyzed using the optical computing devices, the more accurately the properties of the given fluid and/or component will be determined.

The optical computing devices described herein utilize electromagnetic radiation to perform calculations, as opposed to the hardwired circuits of conventional electronic processors. When electromagnetic radiation interacts with a fluid, unique physical and chemical information about the fluid is encoded in the electromagnetic radiation that is reflected from, transmitted through, or radiated from the fluid. This information is often referred to as the spectral "fingerprint" of the fluid. The optical computing devices described herein are capable of extracting the information of the spectral fingerprint of multiple characteristics or analytes within a fluid, and converting that information into a detectable output relating to one or more characteristics of the fluid or a component present within the fluid. That is, through suitable configurations of the optical computing devices, electromagnetic radiation associated with a characteristic or analyte of interest of a fluid can be separated from electromagnetic radiation associated with all other components of the fluid in order to estimate the properties of the fluid in real-time or near real-time.

Figure 1:
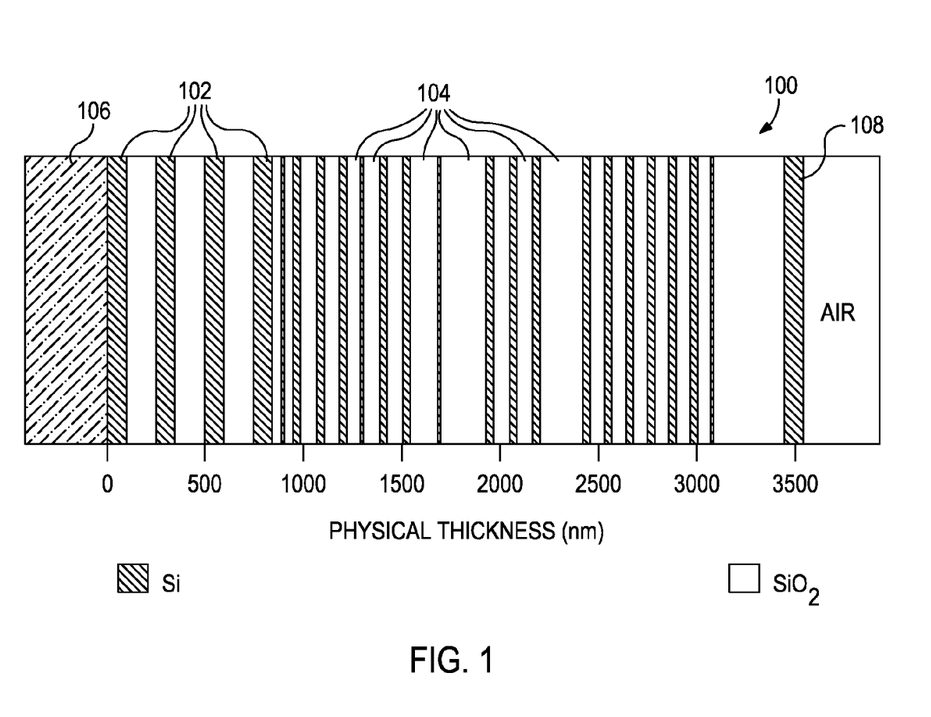
FIG. 1 illustrates an exemplary integrated computation element, according to one or more embodiments.

The processing elements used in the exemplary optical computing devices described herein may be characterized as integrated computational elements (ICE). Each ICE is capable of distinguishing electromagnetic radiation related to the characteristic of interest from electromagnetic radiation related to other components of a fluid. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the fluid using a conventional spectroscopic instrument. The spectrum of interest of a given characteristic typically includes any number of different wavelengths. It should be understood that the exemplary ICE 100 in FIG. 1 does not in fact represent any particular characteristic of a given fluid, but is provided for purposes of illustration only. Consequently, the number of layers 102, 104 and their relative thicknesses, as shown in FIG. 1, bear no correlation to any particular characteristic. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and SiO$_2$) may vary, depending on the application, cost of materials, and/or applicability of the material to the given fluid.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest.

Figure 2:
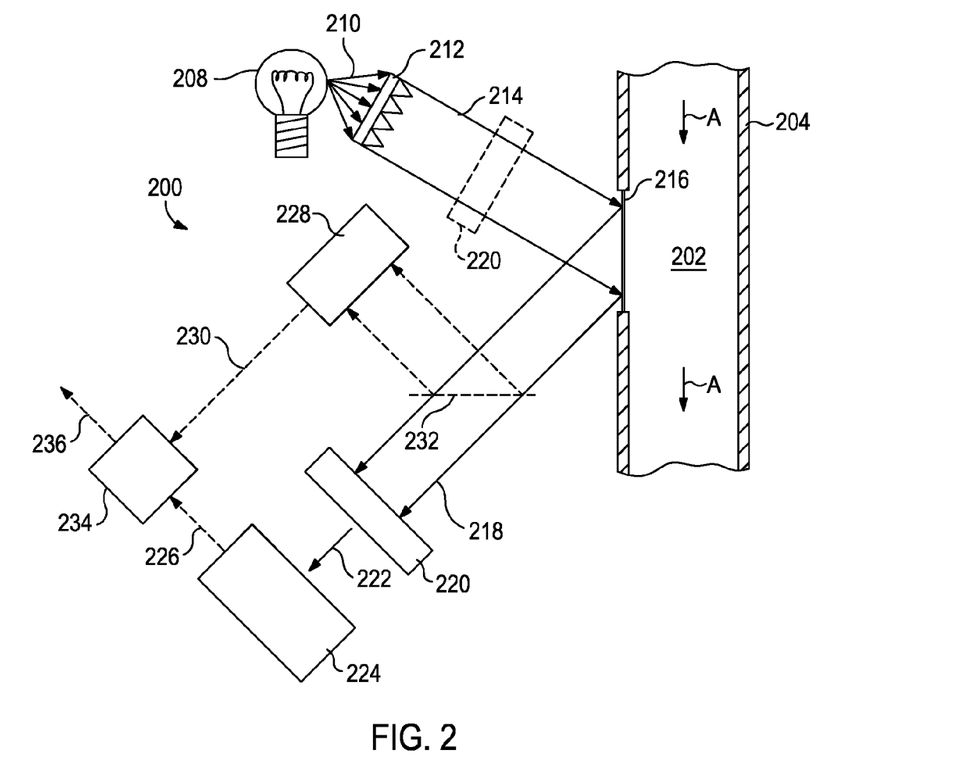
FIG. 2 illustrates an exemplary optical computing device for monitoring a fluid, according to one or more embodiments.

Referring now to FIG. 2, illustrated is an exemplary optical computing device 200 (hereafter "device 200") for monitoring a fluid 202, according to one or more embodiments. In the illustrated embodiment, the fluid 202 may be contained or otherwise flowing within an exemplary flow path 204. The flow path 204 may be a flow line, a pipeline, a wellbore, an annulus defined within a wellbore, or any flow lines or pipelines extending to/from a wellbore. The fluid 202 present within the flow path 204 may be flowing in the general direction indicated by the arrows A. As will be appreciated, however, the flow path 204 may be any other type of flow path, as generally described or otherwise defined herein. For example, the flow path 204 may be a mud pit, a fluid sampling chamber, or any other containment or storage vessel, and the fluid 202 may not necessarily be flowing in the direction A while the fluid 202 is being monitored. As such, portions of the flow path 204 may be arranged substantially vertical, substantially horizontal, or any directional configuration therebetween, without departing from the scope of the disclosure.

The device 200 may be configured to determine a characteristic of interest in the fluid 202, such as the type and/or concentration of a component present within the fluid 202. In some embodiments, the device 200 may include an electromagnetic radiation source 208 configured to emit or otherwise generate electromagnetic radiation 210. The electromagnetic radiation source 208 may be, for example, a light bulb, a light emitting diode (LED), a laser, a blackbody, a photonic crystal, an X-Ray source, combinations thereof, or the like. In some embodiments, a lens 212 may be configured to collect or otherwise receive the electromagnetic radiation 210 and direct a beam 214 of electromagnetic radiation 210 toward the fluid 202. The lens 212 may be any type of optical device configured to transmit or otherwise convey the electromagnetic radiation 210 as desired, such as a normal lens, a Fresnel lens, a diffractive optical element, a holographic graphical element, a mirror (e.g., a focusing mirror), or a type of collimator. In other embodiments, the lens 212 may be omitted from the device 200 and the electromagnetic radiation 210 may instead be directed toward the fluid 202 directly from the electromagnetic radiation source 208.

In one or more embodiments, the device 200 may also include a sampling window 216 arranged adjacent to or otherwise in contact with the fluid 202 for detection purposes. The sampling window 216 may be made from a variety of transparent, rigid or semi-rigid materials that are configured to allow transmission of the electromagnetic radiation 210 therethrough. For example, the sampling window 216 may be made of, but is not limited to, glasses, plastics, semi-conductors, crystalline materials, polycrystalline materials, hot or cold-pressed powders, combinations thereof, or the like. After passing through the sampling window 216, the electromagnetic radiation 210 impinges upon and optically interacts with the fluid 202, including any components present within the fluid 202. As a result, optically interacted radiation 218 is generated by and reflected from the fluid 202. Those skilled in the art, however, will readily recognize that alternative variations of the device 200 may allow the optically interacted radiation 218 to be generated by being transmitted, scattered, diffracted, absorbed, emitted, or re-radiated by and/or from the fluid 202, without departing from the scope of the disclosure.

The optically interacted radiation 218 generated by the interaction with the fluid 202 may be directed to or otherwise be received by an ICE 220 arranged within the device 200. The ICE 220 may be a spectral component substantially similar to the ICE 100 described above with reference to FIG. 1. Accordingly, in operation the ICE 220 may be configured to receive the optically interacted radiation 218 and produce modified electromagnetic radiation 222 corresponding to a particular characteristic of the fluid 202. In particular, the modified electromagnetic radiation 222 is electromagnetic radiation that has optically interacted with the ICE 220, whereby an approximation of the regression vector corresponding to the characteristic of the fluid 202 is obtained.

While FIG. 2 depicts the ICE 220 as receiving reflected electromagnetic radiation from the fluid 202, the ICE 220 may be arranged at any point along the optical train of the device 200, without departing from the scope of the disclosure. For example, in one or more embodiments, the ICE 220 (as shown in dashed) may be arranged within the optical train prior to the sampling window 216 and equally obtain substantially the same results. In other embodiments, the ICE 220 may generate the modified electromagnetic radiation 222 through reflection, instead of transmission therethrough.

Moreover, while only one ICE 220 is shown in the device 200, embodiments are contemplated herein which include the use of at least two ICE 220 cores in the device 200 configured to cooperatively determine the characteristic of interest in the fluid 202. For example, two or more ICE 220 cores may be arranged in series or parallel within the device 200 and configured to receive the optically interacted radiation 218 and thereby enhance sensitivities and detector limits of the device 200. In other embodiments, two or more ICE 220 cores may be arranged on a movable assembly, such as a rotating disc or an oscillating linear array, which moves such that individual ICE 220 cores are able to be exposed to or otherwise optically interact with electromagnetic radiation for a distinct brief period of time. The two or more ICE 220 cores in any of these embodiments may be configured to be either associated or disassociated with the characteristic of interest in the fluid 202. In other embodiments, the two or more ICE 220 cores may be configured to be positively or negatively correlated with the characteristic of interest in the fluid 202.

In some embodiments, it may be desirable to monitor more than one characteristic of interest or component at a time using the device 200. In such embodiments, various configurations for multiple ICE 220 cores can be used, where each ICE 220 core is configured to detect a particular and/or distinct characteristic of interest. In some embodiments, the characteristic can be analyzed sequentially using multiple ICE 220 cores that are provided a single beam of electromagnetic radiation being reflected from or transmitted through the fluid 202. In some embodiments, multiple ICE 220 cores can be arranged on a rotating disc, where the individual ICE 220 cores are only exposed to the beam of electromagnetic radiation for a short time. Advantages of this approach can include the ability to analyze multiple characteristics of the fluid 202 using a single device 200 and the opportunity to assay additional characteristics or components of the drilling fluid simply by adding additional ICE 220 cores to the rotating disc.

In other embodiments, as described in more detail below, multiple optical computing devices can be placed at a single location along the flow path 204, where each optical computing device contains a unique ICE 220 core that is configured to detect a particular characteristic of interest in the fluid 202. In another embodiment, two or more optical computing devices may be arranged in series, such as being located on or within a movable housing configured to perform an analysis at a single location along the length of the flow path 204. In a further embodiment, multiple detection stations, each containing optical computing devices in parallel, can be placed in series for performing a similar analysis.

The modified electromagnetic radiation 222 generated by the ICE 220 may subsequently be conveyed to a detector 224 for quantification of the signal. The detector 224 may be any device capable of detecting electromagnetic radiation, and may be generally characterized as an optical transducer. In some embodiments, the detector 224 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 224 may be configured to produce an output signal 226 in real-time or near real-time in the form of a voltage (or current) that corresponds to the particular characteristic of interest in the fluid 202. The voltage returned by the detector 224 is essentially the dot product of the optical interaction of the optically interacted radiation 218 with the respective ICE 220 as a function of the concentration of the characteristic of interest of the fluid 202. As such, the output signal 226 produced by the detector 224 and the concentration of the characteristic may be related, for example, directly proportional. In other embodiments, however, the relationship may correspond to a polynomial function, an exponential function, a logarithmic function, and/or a combination thereof.

In some embodiments, the device 200 may include a second detector 228, which may be similar to the first detector 224 in that it may be any device capable of detecting electromagnetic radiation. The second detector 228 may be used to detect radiating deviations stemming from the electromagnetic radiation source 208. Undesirable radiating deviations can occur in the intensity of the electromagnetic radiation 210 due to a wide variety of reasons and potentially causing various negative effects on the device 200. In some embodiments, radiating deviations can occur as a result of a build-up of film or material on the sampling window 216 which has the effect of reducing the amount and quality of light ultimately reaching the first detector 224. Without proper compensation, such radiating deviations could result in false readings and the output signal 226 would no longer be primarily or accurately related to the characteristic of interest.

To compensate for these types of undesirable effects, the second detector 228 may be configured to generate a compensating signal 230 generally indicative of the radiating deviations of the electromagnetic radiation source 208, and thereby normalize the output signal 226 generated by the first detector 224. As illustrated, the second detector 228 may be configured to receive a portion of the optically interacted radiation 218 via a beamsplitter 232 in order to detect the radiating deviations. In other embodiments, however, the second detector 228 may be arranged to receive electromagnetic radiation from any portion of the optical train in the device 200 in order to detect the radiating deviations, without departing from the scope of the disclosure.

In some applications, the output signal 226 and the compensating signal 230 may be conveyed to or otherwise received by a signal processor 234 communicably coupled to both the detectors 224, 228. The signal processor 234 may be a computer including a processor and a machine-readable storage medium having instructions stored thereon, which, when executed by the processor 234, cause the device 200 to perform a number of operations, such as determining one or more characteristics of interest of the fluid 202. For instance, the concentration of each characteristic detected with the device 200 can be fed into an algorithm operated by the signal processor 234. The algorithm can be part of an artificial neural network configured to use the concentration of each detected characteristic in order to evaluate the overall characteristic(s) or quality of the fluid 202.

The signal processor 234 may also be configured to computationally combine the compensating signal 230 with the output signal 226 in order to normalize the output signal 226 in view of any radiating deviations detected by the second detector 228. Computationally combining the output and compensating signals 226, 230 may entail computing a ratio of the two signals 226, 230. For example, the concentration or magnitude of each characteristic determined using the device 200 can be fed into an algorithm run by the signal processor 234. The algorithm may be configured to make predictions on how the characteristics of the fluid 202 change if the concentrations of one or more components or additives are changed relative to one another.

In real-time or near real-time, the signal processor 234 may be configured to provide a resulting output signal 236 corresponding to the one or more characteristics of interest in the fluid 202 measured by the one or more ICE 220 cores within the device 200. The resulting output signal 236 may be readable by an operator who can consider the results and make proper adjustments or take appropriate action, if needed. In some embodiments, the resulting signal output 236 may be conveyed, either wired or wirelessly, to the operator for consideration. In other embodiments, the resulting output signal 236 may be recognized by the signal processor 234 as being within or without a predetermined or preprogrammed range of suitable operation and may alert the operator of an out of range reading so appropriate corrective action may be taken, or otherwise autonomously undertake the appropriate corrective action such that the resulting output signal 236 returns to a value within the predetermined or preprogrammed range of suitable operation.

Figure 3:
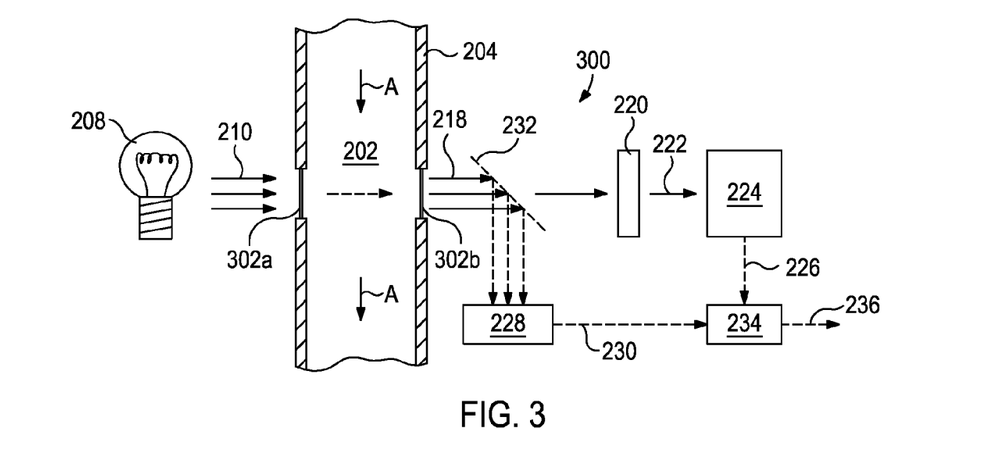
FIG. 3 illustrates another exemplary optical computing device for monitoring a fluid, according to one or more embodiments.

Referring now to FIG. 3, illustrated is another exemplary optical computing device 300 for monitoring the fluid 202, according to one or more embodiments. The optical computing device 300 (hereafter "device 300") may be similar in some respects to the device 200 of FIG. 2, and therefore may be best understood with reference thereto where like numerals indicate like elements that will not be described again. Similar to the device 200, the device 300 may be configured to determine the concentration of a characteristic of interest in the fluid 202 as contained within the flow path 204. Unlike the device 200 of FIG. 2, however, the device 300 in FIG. 3 may be configured to transmit the electromagnetic radiation 210 through the fluid 202 via a first sampling window 302*a* and a second sampling window 302*b* arranged radially-opposite the first sampling window 302*a* on the flow path 204. The first and second sampling windows 302*a,b* may be similar to the sampling window 216 described above in FIG. 2 and therefore will not be described again.

As the electromagnetic radiation 210 passes through the fluid 202 via the first and second sampling windows 302*a,b*, it optically interacts with the fluid 202 and optically interacted radiation 218 is subsequently directed to or otherwise received by the ICE 220 as arranged within the device 300. It is again noted that, while FIG. 3 depicts the ICE 220 as receiving the optically interacted radiation 218 as transmitted through the sampling windows 302*a,b*, the ICE 220 may equally be arranged at any point along the optical train of the device 300, without departing from the scope of the disclosure. For example, in one or more embodiments, the ICE 220 may be arranged within the optical train prior to the first sampling window 302*a* and equally obtain substantially the same results. In yet other embodiments, the ICE 220 may generate the modified electromagnetic radiation 222 through reflection, instead of transmission therethrough. As with the device 200 of FIG. 2, embodiments are contemplated herein which include the use of at least two ICE 220 cores in the device 300 configured to cooperatively determine one or more characteristics of interest or components within the fluid 202.

The modified electromagnetic radiation 222 generated by the ICE 220 is subsequently conveyed to the detector 224 for quantification of the signal and generation of the output signal 226 which corresponds to one or more characteristics of interest in the fluid 202. The device 300 may also include the second detector 228 for detecting radiating deviations stemming from the electromagnetic radiation source 208. As illustrated, the second detector 228 may be configured to receive a portion of the optically interacted radiation 218 via the beamsplitter 232 in order to detect the radiating deviations. The output signal 226 and the compensating signal 230 may then be conveyed to or otherwise received by the signal processor 234 which may computationally combine the two signals 230, 226 and provide in real-time or near real-time the resulting output signal 236 corresponding to the characteristic of interest in the fluid 202.

Those skilled in the art will readily recognize that, in one or more embodiments, electromagnetic radiation may be derived from the fluid being analyzed itself, such as the drilling fluid 202, and otherwise derived independent of any electromagnetic radiation source 208 (FIGS. 2 and 3). For example, various substances naturally radiate electromagnetic radiation that is able to optically interact with the ICE 220 core (FIGS. 2 and 3). In some embodiments, for example, the fluid being analyzed may be a blackbody radiating substance configured to radiate heat that may optically interact with the ICE 220 core. In other embodiments, the fluid may be radioactive or chemo-luminescent and, therefore, radiate electromagnetic radiation that is able to optically interact with the ICE 220 core. In yet other embodiments, the electromagnetic radiation may be induced from the fluid by being acted upon mechanically, magnetically, electrically, combinations thereof, or the like. For instance, in at least one embodiment, a voltage may be placed across the fluid in order to induce the electromagnetic radiation. As a result, embodiments are contemplated herein where the electromagnetic radiation source 208 is omitted from the optical computing devices described herein.

Figure 4:
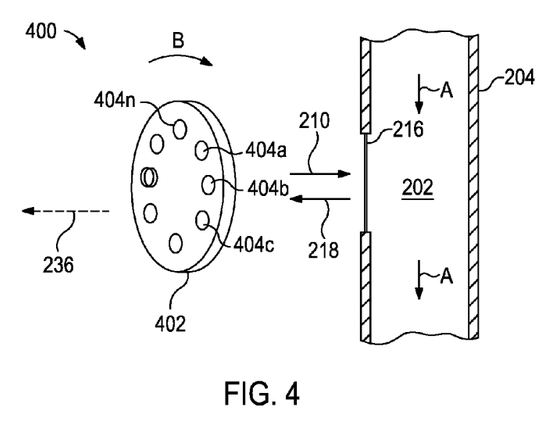
FIG. 4 illustrates an optical computing device array configuration for monitoring a fluid, according to one or more embodiments.

Referring now to FIG. 4, with continued reference to FIGS. 1-3, an optical computing device array 400 is illustrated, according to one or more embodiments. The optical computing device array 400 may include one or more optical computing devices 404 (shown as optical computing devices 404*a*, 404*b*, 404*c*, . . . 404*n*) arranged on or within a rotatable or movable housing 402. Each optical computing device 404*a-n* (hereafter "device 404*a-n*") of the array 400 may be similar to the device 200 of FIG. 2, and thus may best be understood with reference thereto, where like numerals indicate elements that will not be described again. Each device 404*a-n* may be configured to optically interact with and determine one or more characteristics of interest of the fluid 202 within the flow path 204.

In one or more embodiments, the movable housing 402 may be of any general shape. For example, as illustrated, the movable housing 402 may be generally circular and configured to rotate about a central axis at a predetermined frequency or speed during operation. In other embodiments, however, the movable housing 402 may be generally square or rectangular (e.g., polygonal) and the devices 404*a-n* may be arranged adjacent each other in a generally linear relationship. In operation, such a movable housing 402 may be configured to move or otherwise oscillate in a linear path at a predetermined oscillation speed and the devices 404*a-n* may be arranged, for example, in horizontal, vertical, or diagonal rows.

As depicted in FIG. 4, the movable housing 402 is substantially-disc-shaped and may be configured to rotate in a first direction, indicated by the arrow B. It will be appreciated, however, that the movable housing 402 may equally be able to rotate in a second direction opposite the direction B, without departing from the scope of the disclosure. The devices 404*a-n* may be arranged or otherwise disposed about the periphery of the movable housing 402, being circumferentially-spaced from each other. As arranged in the movable housing 402, each device 404*a-n* may be configured to rotationally move in a preset angular detection path at a predetermined speed.

Each of the devices 404*a-n* may transmit electromagnetic radiation 210 through the sampling window 216 to optically interact with the fluid 202. Optically interacted radiation 218 may then be reflected back towards the array 400 for processing. After the devices 404*a-n* receive the optically interacted radiation 218, the devices 404*a-n* may then generate corresponding resulting output signals 236 related to the component or characteristic of interest measured. In one embodiment, the movable housing 402 may include a central computer (not shown) configured to receive and process each resulting output signal 236 and deliver or otherwise provide a collective output signal (not indicated).

In one embodiment, each of the devices 404*a-n* may be configured to monitor only a single component of the downhole fluid 202. Advantageously, additional components of the fluid 202 may be analyzed by adding additional devices 404*a-n* to the movable housing 402 and/or increasing the number of ICE 220 (FIG. 2) cores used within each device 404*a-n*. It should be appreciated that as the number of ICE 220 cores or devices 404*a-n* increases, related additional outputs signals may be included in the depicted output signals 236 of FIG. 4.

Figure 5:
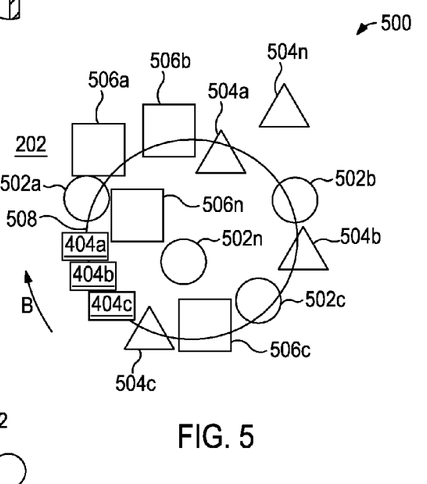
FIG. 5 illustrates a schematic diagram of the detection path of the optical computing device array of FIG. 4, according to one or more embodiments.

Referring now to FIG. 5, with continued reference to FIG. 4, illustrated is a schematic diagram 500 depicting an exemplary detection path 508 of the array 400 of FIG. 4 as each device 404*a-n* optically interacts with the downhole fluid 202, according to one or more embodiments. More particularly, the diagram 500 depicts individual particles or components 502, 504, 506 (shown as components 502*a-n*, 504*a-n*, 506*a-n*) present within or otherwise forming part of the downhole fluid 202. Each type of component 502*a-n*, 504*a-n*, 506*a-n* may be different in size or morphology (e.g., shape). For example, each particle of the first type of component 502*a-n* may be of the same specie or characteristic, but may exhibit a different size or shape from the other particles of the same characteristic. Likewise, each particle of the second type of component 504*a-n* may be of the same specie or characteristic, but may exhibit a different size or shape from the other particles of the same characteristic, and each particle of the third type of component 506*a-n* may be of the same specie or characteristic, but may exhibit a different size or shape from the other particles of the same characteristic.

The diagram 500 further depicts the optical computing devices 404*a*, 404*b*, and 404*c* of the array 400 (FIG. 4) arranged about the detection path 508. As illustrated, the devices 404*a-c* are configured to follow the detection path 508 as they are rotated by the movable housing 402 depicted in FIG. 4. In other embodiments, where the movable housing 402 encompasses a linear array of devices 404*a-n*, for example, the devices 404*a-c* would be configured to follow a linear detection path (not shown). As the devices 404*a-c* of FIG. 5 move in the detection path 508 and optically interact with the components 502*a-n*, 504*a-n*, 506*a-n*, each device 404*a-c* may generate corresponding output signals related to the characteristics that each is configured to detect. More particularly, the first optical computing device 404*a* may be configured to detect the first type of components 502*a-n*, the second optical computing device 404*b* may be configured to detect the second type of components 504*a-n*, and the third optical computing device 404*c* may be configured to detect the third type of components 506*a-n*.

Figure 6:
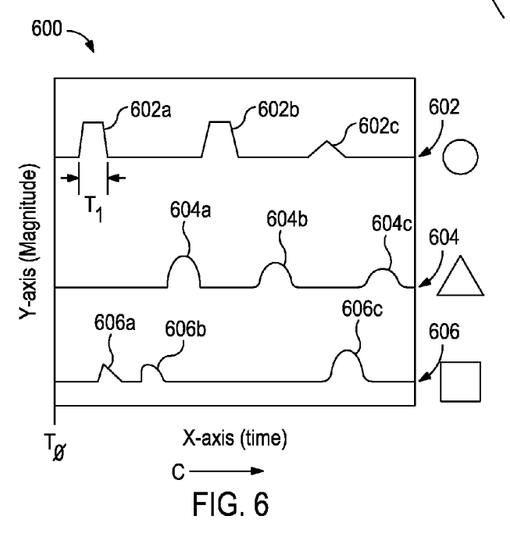
FIG. 6 depicts a graphical illustration of exemplary output signals of the optical computing device array of FIG. 4, according to one or more embodiments.

For example, referring now to FIG. 6, with continued reference to FIG. 5, illustrated is a graph 600 that depicts exemplary output signals 602, 604, and 606 corresponding to the devices 404*a-c* of FIG. 5, according to one or more embodiments. More specifically, the first output signal 602 may correspond to output signals derived from the first device 404*a*, the second output signal 604 may correspond to output signals derived from the second device 404*b*, and the third output signal 606 may correspond to output signals derived from the third device 404*c*. As will be appreciated, each output signal 602, 604, 606 may be similar to the output signals 236 described above, thereby each indicating or otherwise representing a concentration of a particular characteristic of interest as detected by its associated optical computing device 404*a-c*.

The X-axis of the graph 600 represents time of detection, increasing in the direction C. The Y-axis of the graph 600 represents the magnitude of each output signal 602, 604, 606, where increases in signal magnitude represent detection of a corresponding component 502*a-n*, 504*a-n*, 506*a-n* within the fluid 202 by the devices 404*a-c*. One of skill in the art will appreciate that scaling may or may not be applied when plotting the output signals 602, 604, 606. As depicted, the output signals 602, 604, 606 are plotted at various offsets on the Y-axis starting from time $t_0$, where the value for each output signal 602, 604, 606 is essentially zero, indicating that none of the devices 404*a-c* detect or otherwise sense a corresponding component 502*a-n*, 504*a-n*, 506*a-n* at that moment.

In exemplary operation, and with continued reference to FIG. 5, as the first device 404*a* rotates in the direction B, it may first optically interact with the component 502*a*, which encompasses a characteristic that the first device 404*a* is configured to detect. As a result, a magnitude increase may be generated in the corresponding output signal 602, shown as output signal 602*a*. Continuing along the detection path 508 in direction B, the magnitude of the output signal 602*a* will eventually decrease back to a magnitude of essentially zero as the component 502*a* is no longer detected by the first device 404*a*. As the first device 404*a* continues along the detection path 508, it eventually optically interacts with the component 506*a*. However, as the first device 404*a* is not configured to detect component 506*a*, the magnitude of the output signal 602 remains substantially unchanged (i.e., remains at approximately zero). Similar results occur as the first device 404*a* interacts with any of components 504*a-n* and 506*a-n*.

However, the output signal 602 will register magnitude increases as the first device 404*a* optically interacts with any of the particles of component 502*a-n* as it travels along the detection path 508. Such magnitude increases are illustrated in the graph 600 as output signals 602*b* and 602*c*, as the first device 404*a* optically interacts with components 502*b* and 502*c*, respectively, as shown in the diagram 500 of FIG. 5.

The second and third devices 404*b* and 404*c* may operate similarly, thereby registering corresponding magnitude increases in their corresponding output signals 604, 606, respectively, when each device 404*b,c* optically interacts with a component that it is configured to detect. More particularly, the second output signal 604 in the graph 600 depicts magnitude increases 604*a*, 604*b*, and 604*c*, corresponding to optical interaction of the second device 404*b* with the components 504a, 504b, and 504c, respectively. Similarly, the third output signal 606 in the graph 600 depicts magnitude increases 606a, 606b, and 606c, corresponding to optical interaction of the third device 404c with the components 506a, 506b, and 506c, respectively.

In one embodiment, the devices 404a-n (FIG. 4) may be configured to determine or otherwise calculate particle chord length and particle size distribution (PSD) of the components 502a-n, 504a-n, 506a-n within the fluid 202. As well known to one of skill in the art, the chord length of a component or particle may be defined as the straight-line distance from one edge of a particle to another. Thus, the duration of reflection measured is a "chord." For example, the chord length for component particle 502a approximately corresponds to the detection time required for the first device 404a to detect the particle 502a from one edge of the particle 502a to the other. As indicated in the graph 600, this is depicted as a time period of $T_1$. More particularly, the time period of $T_1$ represents the period of time the first device 404a measured the particle 502a as it moved in the detection path 508. Using the known and predetermined angular rotation (e.g., speed) of the movable housing 402, in conjunction with now known detection time, the approximate chord length for the particle 502a may then be determined.

As the chord length may vary depending on the shape and orientation of the particles, thousands of individual chord lengths are typically measured over a predetermined period of time to produce a "chord length distribution." In another embodiment, the measured chord lengths and chord length distributions may be used to determine PSD according to any of a plurality of calculation algorithms and methods known to those skilled in the art.

A distinguishing feature of the present disclosure is the well operator's knowledge of the aforementioned measurements and calculations with respect to a particular component (e.g., components 502a-n, 504a-n, 506a-n) of the fluid 202. Current technologies may perform chord length measurements on particles within a drilling fluid. However, these measurements fail to definitively relate the chord length to a particular component 502a-n, 504a-n, 506a-n of the drilling fluid 202. As disclosed herein, however, the use of at least one ICE 220 core (FIG. 2) within the devices 404a-c results in the output signal (e.g., 602, 604, 606) being directly related to a specific component 502a-n, 504a-n, 506a-n or other characteristic of the drilling fluid 202. Accordingly, measurements and calculations such as chord length and PSD are knowingly related to a particular component 502a-n, 504a-n, 506a-n of the fluid 202.

For instance, in at least one embodiment, the devices 404a-n (FIG. 4) may be configured to monitor and calculate concentrations or loss of LCM or other additives within the fluid 202. Currently, knowledge of component 502a-n, 504a-n, 506a-n quantities and ratios is based on particle size distribution within the fluid 202. However, as generally described above, the presently described devices 404a-n may be configured to provide the relative concentration of products, such as LCM or other common additives, thus enabling a real-time determination of individual component 502a-n, 504a-n, 506a-n concentration and/or loss. As the number of component particles 502a-n, 504a-n, 506a-n within the fluid 202 may be calculated by counting corresponding magnitude spikes (e.g., output signal 602a,b,c) over a period of time, concentration and/or loss of a particular products, such as LCM or other common drilling fluid additives, may be calculated in real-time by taking the difference of particle count at two known points in time.

In one or more additional embodiments, the general morphology (e.g., shape) of the particles of each component 502a-n, 504a-n, 506a-n may be estimated based off the output signals 602, 604, 606. For example, the response shape of each output signal 602, 604, 606 (i.e., the slope, curvature, and/or rate of increase and decrease) may be indicative of the general shape of the particle of each component 502a-n, 504a-n, 506a-n being detected. As depicted, the output signals 602a-c from the first optical computing device 404a generally have sharp rates of increase and decrease in magnitude, thus possibly indicating the measured particles associated with the component 502a-n are generally circular in shape. In another example, the magnitude rate of increase and decrease for the output signals 604a-c from the second optical computing device 404b are generally gradual or curved in nature, thus possibly indicating the measured particles associated with the component 504a-n are generally square or a shape with sharp edges. As the particle components 502a-n, 504a-n, 506a-n break and change shape during circulation, knowledge of the shape of the particles may assist a well operator in determining the best additives to use for a particular well.

One of skill in the art will appreciate that FIGS. 5 and 6 are for illustrative purposes only and should be not be read as limiting the present disclosure. For example, the fluid 502 of FIG. 5 may contain more or less particles or components 502a-n, 504a-n, 506a-n, without departing from the scope of the disclosure. Further, the output signals 602, 604, 606 of the graph 600, and their corresponding magnitudes 602a-c, 604a-c, 606a-c, should not be interpreted as being drawn to scale, either in time, voltage, or curvature, in relation to the particles or components 502a-n, 504a-n, 506a-n.

Figure 7:
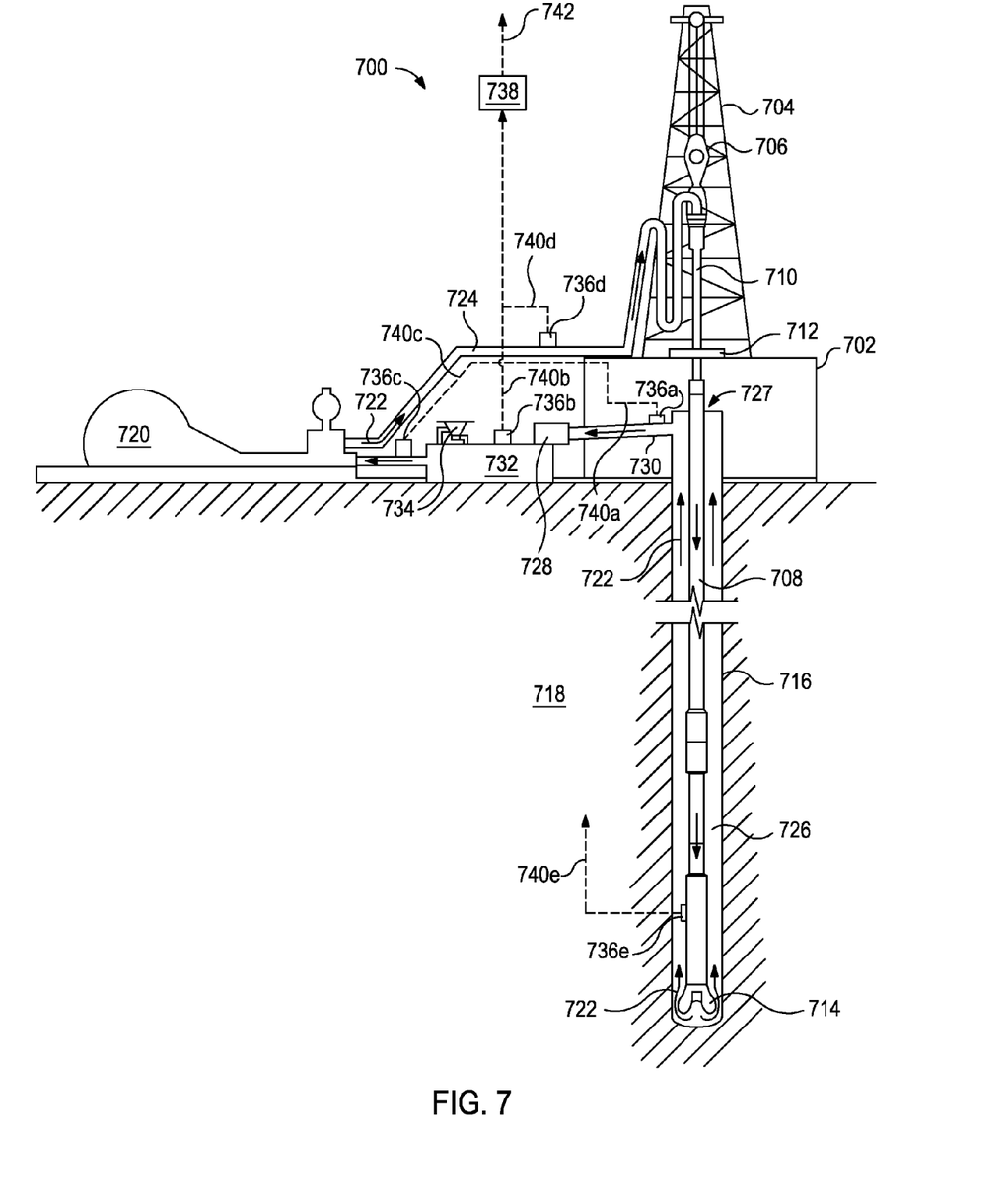
FIG. 7 illustrates an exemplary wellbore drilling assembly that may employ one or more optical computing devices for monitoring a fluid, according to one or more embodiments.

Referring now to FIG. 7, illustrated is an exemplary wellbore drilling assembly 700 that may employ one or more optical computing devices or optical computing device arrays described herein in order to monitor a drilling fluid or a completion fluid, according to one or more embodiments. The drilling assembly 700 may include a drilling platform 702 that supports a derrick 704 having a traveling block 706 for raising and lowering a drill string 708. A kelly 710 supports the drill string 708 as it is lowered through a rotary table 712. A drill bit 714 is attached to the distal end of the drill string 708 and is driven either by a downhole motor and/or via rotation of the drill string 708 from the well surface. As the bit 714 rotates, it creates a borehole 716 that penetrates various subterranean formations 718.

A pump 720 (e.g., a mud pump) circulates drilling fluid 722 through a feed pipe 724 and to the kelly 710, which conveys the drilling fluid 722 downhole through an interior conduit defined in the drill string 708 and through one or more orifices in the drill bit 714. The drilling fluid 722 is then circulated back to the surface via an annulus 726 defined between the drill string 708 and the walls of the borehole 716. The drilling fluid 722 serves several purposes, such as providing hydrostatic pressure to prevent formation fluids from entering into the borehole 716 and keeping the drill bit 714 cool and clean during drilling. The drilling fluid 722 also serves to carry drill cuttings and solids out of the borehole 716 and suspend the drill cuttings and solids while drilling is paused and/or when the drill bit 714 is brought in and out of the borehole 716.

As the spent drilling fluid 722 returns to the surface, it may exit the annulus 726 at the wellhead 727 and may be conveyed to one or more drilling fluid rehabilitation devices, such as solids control equipment 728, via the interconnecting flow line 730. The solids control equipment 728 may include one or more centrifuges, filters, and/or other separation devices configured to substantially remove the drill cuttings, solids, and/or LCM from the drilling fluid 722 and deposit a cleaned drilling fluid 722 into a nearby retention pit 732 (i.e., a mud pit).

Several additives or components may be added to the drilling fluid 722 in order to maintain the drilling fluid 722 in proper working order and otherwise enhance drilling capabilities. In some embodiments, the additives and components may be added to the drilling fluid 722 via a mixing hopper 734 fluidly coupled to the retention pit 732. The rehabilitated drilling fluid 722 may then be recirculated and pumped back into the borehole 716 with the pump 720 via the feed pipe 724.

The drilling fluid 722 may be maintained in proper working order if the depletion rate of the components is counteracted with proper fluid treatment or management. Accordingly, knowing the proper and correct treatment rate in real-time may be useful in optimizing the drilling fluid 722. To accomplish this, one or more optical computing devices 736 (shown as optical computing devices 736a-e) may be included at various points throughout the drilling assembly 700 in order to monitor the drilling fluid 722 and/or one or more components present within the drilling fluid 722. The optical computing devices 736a-e (hereafter "devices 736a-e) may be substantially similar to at least one of the devices 200, 300 of FIGS. 2 and 3, respectively, or arranged similar to the optical computing device array 400 of FIG. 4, and therefore will not be described again in detail. In exemplary operation, the devices 736a-e may be configured to measure and report the real-time characteristics of the drilling fluid 722, which may provide an operator with real-time data useful in adjusting various drilling parameters in order to optimize drilling operations.

In some embodiments, for example, a first device 736a may be arranged to monitor the drilling fluid 722 as it is recirculated or otherwise exits out of the borehole 716. As illustrated, the first device 736a may be arranged on or otherwise coupled to the flow line 730, thereby being able to monitor the drilling fluid 722 once it exits the annulus 726 at the wellhead 727. If initial concentrations or amounts of components were known prior to conveying the drilling fluid 722 into the borehole 716, the first device 736a may be useful in providing real-time data indicative of how much component depletion the drilling fluid 722 underwent after being circulated through the borehole 716.

In other embodiments, a second device 736b may be arranged on or otherwise in optical communication with the retention pit 732. The second device 736b may be configured to monitor the drilling fluid 722 after it has undergone one or more treatments in the solids control equipment 728, thereby providing a real-time concentration of components remaining in the drilling fluid 722. In some embodiments, the second device 736b may also be configured to monitor the drilling fluid 722 in the retention pit 732 as additional additive components are being added or otherwise mixed into the drilling fluid 722 via the mixing hopper 734. For instance, the second device 736b may be able to report to an operator when a predetermined amount or proper level of a particular additive component has been added to the drilling fluid 722 such that the performance of the drilling fluid 722 would be optimized. As will be appreciated, such real-time measurement avoids unnecessarily over-treating the drilling fluid 722, thereby saving time and costs.

In yet other embodiments, a third device 736c may be arranged in the drilling assembly 700 following the retention pit 732, but prior to the mud pump 720. Alternatively, or in addition thereto, a fourth device 736d may be arranged in the drilling assembly 700 following the mud pump 720, such as being arranged at some point along the feed pipe 724. The third and/or fourth devices 736c,d may be useful in confirming whether adequate amounts or concentrations of components have been added to the drilling fluid 722 and otherwise determine whether the drilling fluid 722 is at optimal or predetermined levels for adequate drilling operations. In other embodiments, the third and/or fourth devices 736c,d may be useful in providing an initial reading of characteristics of the drilling fluid 722, including concentrations of any components found therein, prior to the drilling fluid 722 being conveyed into the borehole 716. Such an initial reading may be compared with the resulting signal provided by the first device 736a such that a determination of how much of a particular component remains in the drilling fluid 722 after circulation through the borehole 716, as briefly mentioned above.

In some embodiments, the drilling assembly 700 may further include a fifth device 736e arranged downhole in the borehole 716 and configured to monitor the drilling fluid 722 within the annulus 726. It should be noted that while the fifth device 736e is illustrated as a single device, it is contemplated herein to include any number of devices arranged within the borehole 716 to monitor the drilling fluid 722. Moreover, while the fifth device 736e is shown as being coupled at or near the drill bit 714, those skilled in the art will readily appreciate that the fifth device 736e, and any number of other devices, may be arranged at any point along the drill string 708, without departing from the scope of the disclosure.

The devices 736a-e may be communicably coupled to a signal processor 738 and configured to convey corresponding output signals 740a-e thereto. The signal processor 738 may be similar to the signal processor 234 of FIGS. 2 and 3, and therefore will not be described again in detail. The signal processor 738 may employ an algorithm configured to calculate or otherwise determine any differences between any two or more of the output signals 740a-e. For example, the first output signal 740a may be indicative of a concentration of a component in the drilling fluid 722 or other characteristic of the fluid 722 at the location of the first device 736a, the second output signal 740b may be indicative of the concentration of the component or other characteristic of the fluid 722 at the location of the second device 736b, and so on. Accordingly, the signal processor 738 may be configured to determine how the concentration of the component and/or the magnitude of the characteristic of interest in the fluid 722 has changed between each monitoring location.

In real-time or near real-time, the signal processor 738 may be configured to provide a resulting output signal 742 corresponding to one or more characteristics of the fluid. In some embodiments, the resulting output signal 742 may provide a measured difference in the component and/or the magnitude of the characteristic of interest in the fluid 722. In some embodiments, the resulting output signal 742 may be conveyed, either wired or wirelessly, to an operator for consideration. In other embodiments, the resulting output signal 742 may be recognized by the signal processor 738 as being within or without a predetermined or preprogrammed range of suitable operation for the drilling fluid 722. If the resulting output signal 742 exceeds the predetermined or preprogrammed range of operation, the signal processor 738 may be configured to alert the operator so appropriate corrective action may be taken on the drilling fluid 722. Otherwise, the signal processor 738 may be configured to autonomously undertake the appropriate corrective action such that the resulting output signal 742 returns to a value within the predetermined or preprogrammed range of suitable operation. At least one corrective action that may be undertaken may include adding additives or components to the drilling fluid 722 via, for example, the mixing hopper 734.

Still referring to FIG. 7, one or more of the devices 736a-e may be configured to help optimize operating parameters for the solids control equipment 728. The solids control equipment 728 may include, but is not limited to, one or more of a shaker (e.g., shale shaker), a centrifuge, a hydrocyclone, a separator, a desilter, a desander, combinations thereof, and the like. In other embodiments, the solids control equipment 728 may further include one or more separators operating with magnetic fields or electric fields, without departing from the scope of the disclosure. As briefly mentioned above, the solids control equipment 728 may be configured to substantially remove the drill cuttings and other unwanted solid particulates from the drilling fluid 722, thereby depositing a "cleaned" or substantially cleaned drilling fluid 722 into the retention pit 732.

One common problem encountered with typical solids control equipment 728 is the inefficient removal of solids and other particulates. For example, when solids control equipment 728 are not properly tuned, they can sometimes pass unwanted solids or other contaminating particulates into the retention pit 732, thereby providing a less effective drilling fluid 722 to be recirculated back into the borehole 716. In other cases, un-tuned solids control equipment 728 may inadvertently remove valuable additive components or materials, such as LCM or the like, from the drilling fluid 722, likewise having an adverse effect on the performance of the drilling fluid 722.

To help avoid this problem, the first and second devices 736a,b may be configured to monitor the inlet and outlet of the solids control equipment 728, respectively, thereby providing an operator with a real-time indication of the efficiency of the solids control equipment 728. Specifically, the first device 736a may be configured to monitor the drilling fluid 722 before or while it is introduced into the solids control equipment 728, and the second device 736b may be configured to monitor the drilling fluid 722 after it has undergone one or more processes or treatments in the solids control equipment 728 or otherwise as it is being discharged therefrom.

The output signals 740a,b derived from each device 736a,b, respectively, may provide the operator with valuable data regarding the chemical and physical conditions of the drilling fluid 722 before and after the solids control equipment 728. For instance, in some embodiments, the second output signal 740b may provide the operator with one or more characteristics of the drilling fluid 722 as it exits the solids control equipment 728. As such, the second output signal 740b may verify that particular components of interest are present within the drilling fluid 722 and thereby serve as a quality control measure for the drilling fluid 722. When concentrations of one or more components are not at their ideal levels, adjustments to the contents of the drilling fluid 722 may be undertaken in response.

In some embodiments, the output signals 740a,b may be conveyed to the signal processor 738 and its resulting output signal 742 may provide the operator with a qualitative and/or quantitative comparison of the first and second output signals 740a,b, thereby providing valuable information as to the effectiveness of the solids control equipment 728. In some embodiments, for example, the first and second devices 736a,b may be configured to monitor components and/or substances in the drilling fluid 722 such as solid particulates, clays (e.g., smectite, illite, kaolin, etc.), graphitized coke, and weighting materials (e.g., barite), which are typically removed from the drilling fluid 722 in the various solids control equipment 728. By comparing the second output signal 740b with the first output signal 740a, it may be determined as to whether the solids control equipment 728 is adequately removing the components and/or substances of interest, or whether it may be beneficial to adjust one or more parameters of the solids control equipment 728.

In some embodiments, individual optical computing devices (not shown) may be placed at the inlet and/or outlet of each of the devices used in the solids control equipment 728. For example, if applicable to the particular application, one or more optical computing devices may be placed at the inlet and/or outlet of each shaker, centrifuge, hydrocyclone, separator, desilter, and/or desander used in the solids control equipment 728. As a result, the operator may be provided with data as to the efficiency of each individual component device of the solids control equipment 728, thereby allowing for the strategic fine-tuning of each individual piece of equipment or at least the individual equipment responsible for the reported inefficiencies.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Embodiments disclosed herein include:

A. A system that includes a flow path containing a fluid having at least one component present therein, and a movable housing having at least one optical computing device configured to move with the movable housing along a detection path, the at least one optical computing device including at least one integrated computational element (ICE) configured to optically interact with the fluid over the detection path, wherein the at least one ICE is configured to detect a characteristic of the at least one component and generate an output signal corresponding to the characteristic.

B. A method of containing a fluid within a flow path, the fluid including at least one component present therein, optically interacting at least one integrated computational element (ICE) with the at least one component over a detection path, the ICE and the at least one component moving relative to one another and the ICE being configured to detect a characteristic of the at least one component, and wherein the ICE is an integral part of an optical computing device arranged on a movable housing that is capable of moving along the detection path, determining the characteristic of the at least one component with the at least one optical computing device, and generating an output signal corresponding to the characteristic of the at least one component.

C. A method of containing a fluid within a flow path that provides at least a first monitoring location and a second monitoring location, the fluid having at least one component present therein, generating a first output signal corresponding to a characteristic of the at least one component at the first monitoring location with a first optical computing device, the first optical computing device being arranged on a first movable housing configured to move the first optical computing device along a first detection path, and the first optical computing device having a first integrated computational element (ICE) configured to optically interact with the fluid and thereby convey optically interacted light to a first detector which generates the first output signal, generating a second output signal corresponding to a characteristic of the at least one component at the second monitoring location with a second optical computing device, the second optical computing device being arranged on a second movable housing configured to move the second optical computing device along a second detection path, and the second optical computing device having a second ICE configured to optically interact with the fluid and thereby convey optically interacted light to a second detector which generates the second output signal, receiving the first and second output signals with a signal processor, and determining a difference between the first and second output signals with the signal processor.

Each of embodiments A, B, and C may have one or more of the following additional elements in any combination: Element 1: wherein the fluid is a drilling fluid. Element 2: wherein the flow path is at least one of a flow line, a pipeline, production tubing, drill string, work string, casing, a wellbore, an annulus defined between a wellbore and any tubular arranged within the wellbore, a subterranean formation, a mud pit, a containment or storage vessel, and a sampling chamber. Element 3: wherein the at least one component comprises a lost circulation material selected from the group consisting of sand, shale, ground marble, bauxite, ceramic materials, glass materials, metal pellets, high strength synthetic fibers, resilient graphitic carbon, cellulose flakes, wood, resins, polymer materials, polytetrafluoroethylene materials, nut shell pieces, seed shell pieces, fruit pit pieces, and composite materials. Element 4: wherein the at least one component comprises at least one of a gelling agent, an emulsifier, proppants or other solid particulates, a clay control agent, a clay stabilizer, a clay inhibitor, a chelating agent, a flocculant, a viscosifier, a weighting material, a base fluid, and a rheology control agent. Element 5: wherein the characteristic of the component is at least one of chemical composition, phase, impurity content, pH, alkalinity, viscosity, density, particle size, particle size distribution, particle morphology, particle shape, chord length of particles, ionic strength, total dissolved solids, salt content, porosity, opacity, bacteria content, total hardness, combinations thereof, and state of matter. Element 6: wherein the movable housing is polygonal and the at least one optical computing device is arranged linearly, and wherein the detection path is linear. Element 7: wherein the movable housing is disc-shaped and the at least one optical computing device is disposed about a periphery of the movable housing, and wherein the detection path is circular. Element 8: wherein the movable housing moves at a predetermined speed along the detection path. Element 9: further comprising a signal processor associated with the at least one optical computing device, the signal processor being configured to provide a resulting output signal corresponding to the characteristic of the at least one component detected by the least one ICE. Element 10: further comprising a central computer in communication with the at least one optical computing device and configured to receive the resulting output signal from the at least one optical computing device and generate a collective output signal.

Element 11: wherein determining the characteristic of the at least one component further comprises determining a concentration of the at least one component in the fluid. Element 12: wherein determining the characteristic of the at least one component further comprises determining at least one of a particle chord length, a particle chord length distribution, a particle morphology, a particle shape, a particle size, and a particle size distribution of the at least one component within the fluid. Element 13: further comprising moving the movable housing at a predetermined rate. Element 14: wherein the at least one optical computing device comprises a first optical computing device and a second optical computing device arranged on the movable housing, the method further comprising generating a first resulting output signal from the first optical computing device, wherein the first optical computing device has a first ICE configured to detect a first characteristic of the at least one component and the first resulting output signal corresponds to the first characteristic of the at least one component, generating a second resulting output signal from the second optical computing device, wherein the second optical computing device has a second ICE configured to detect a second characteristic of the at least one component and the second resulting output signal corresponds to the second characteristic of the at least one component, and generating a cumulative output signal from a central computer in communication with the first and second optical computing devices, the cumulative output signal including the first and second resulting output signals.

Element 15: wherein determining the difference between the first and second output signals further comprises determining how the characteristic of the at least one component changed between the first and second monitoring locations. Element 16: wherein the characteristic of the at least one component is a concentration of the at least one component in the fluid, the method further comprising determining the characteristic of the at least one component at the first monitoring location with the first optical computing device, and determining the characteristic of the at least one component at the second monitoring location with the second optical computing device. Element 17: wherein the characteristic of the at least one component is at least one of a particle chord length, a particle chord length distribution, a particle morphology, a particle shape, a particle size, and a particle size distribution of the at least one component within the fluid, the method further comprising determining the characteristic of the at least one component at the first monitoring location with the first optical computing device, and determining the characteristic of the at least one component at the second monitoring location with the second optical computing device.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A system comprising:
    a flow path containing a fluid having at least one component present therein; and
    a movable housing having at least one optical computing device coupled thereto to move with the movable housing along a detection path, the at least one optical computing device including at least one integrated computational element (ICE) that optically interacts with the fluid along the detection path,
    wherein the at least one ICE is configured to detect a characteristic of the at least one component and generate an output signal corresponding to the characteristic, and
    wherein the characteristic of the at least one component is selected from the group consisting of particle size, particle size distribution, particle morphology, particle shape, and chord length of the at least one component.

2. The system of claim 1, wherein the fluid is a drilling fluid.

3. The system of claim 2, wherein the flow path is at least one of a flow line, a pipeline, production tubing, drill string, work string, casing, a wellbore, an annulus defined between a wellbore and any tubular arranged within the wellbore, a subterranean formation, a mud pit, a containment or storage vessel, and a sampling chamber.

4. The system of claim 1, wherein the at least one component comprises a lost circulation material selected from the group consisting of sand, shale, ground marble, bauxite, ceramic materials, glass materials, metal pellets, high strength synthetic fibers, resilient graphitic carbon, cellulose flakes, wood, resins, polymer materials, polytetrafluoroethylene materials, nut shell pieces, seed shell pieces, fruit pit pieces, and composite materials.

5. The system of claim 1, wherein the at least one component comprises at least one of a gelling agent, an emulsifier, proppants or other solid particulates, a clay control agent, a clay stabilizer, a clay inhibitor, a chelating agent, a flocculant, a viscosifier, a weighting material, a base fluid, and a rheology control agent.

6. The system of claim 1, wherein the characteristic of the at least one component is further selected from the group comprising chemical composition, phase, impurity content, pH, alkalinity, viscosity, density, ionic strength, total dissolved solids, salt content, porosity, opacity, bacteria content, total hardness, combinations thereof, and state of matter.

7. The system of claim 1, wherein the movable housing is polygonal and the at least one optical computing device is arranged linearly, and wherein the detection path is linear.

8. The system of claim 1, wherein the movable housing is disc-shaped and the at least one optical computing device is disposed about a periphery of the movable housing, and wherein the detection path is circular.

9. The system of claim 1, wherein the movable housing moves at a predetermined speed along the detection path.

10. The system of claim 1, further comprising a signal processor associated with the at least one optical computing device, the signal processor being configured to provide a resulting output signal corresponding to the characteristic of the at least one component detected by the least one ICE.

11. The system of claim 10, further comprising a central computer in communication with the at least one optical computing device and configured to receive the resulting output signal from the at least one optical computing device and generate a collective output signal.

12. A method, comprising:
containing a fluid within a flow path, the fluid including at least one component present therein;
moving an optical computing device along a detection path as coupled to a movable housing, the optical computing device including at least one integrated computational element (ICE);
optically interacting the at least one ICE with the at least one component along the detection path and thereby detecting;
determining the characteristic of the at least one component with the at least one optical computing device; and
generating an output signal corresponding to the characteristic of the at least one component,
wherein the characteristic of the at least one component is selected from the group consisting of particle chord length, particle chord length distribution, particle morphology, particle shape, particle size, and particle size distribution of the at least one component within the fluid.

13. The method of claim 12, wherein determining the characteristic of the at least one component further comprises determining a concentration of the at least one component in the fluid.

14. The method of claim 12, further comprising moving the movable housing at a predetermined rate.

15. The method of claim 12, wherein the at least one optical computing device comprises a first optical computing device and a second optical computing device arranged on the movable housing, the method further comprising:
generating a first resulting output signal from the first optical computing device, wherein the first optical computing device has a first ICE configured to detect a first characteristic of the at least one component and the first resulting output signal corresponds to the first characteristic of the at least one component;
generating a second resulting output signal from the second optical computing device, wherein the second optical computing device has a second ICE configured to detect a second characteristic of the at least one component and the second resulting output signal corresponds to the second characteristic of the at least one component; and
generating a cumulative output signal from a central computer in communication with the first and second optical computing devices, the cumulative output signal including the first and second resulting output signals.

16. A method, comprising:
containing a fluid within a flow path that provides a first monitoring location and a second monitoring location, the fluid having at least one component present therein;
generating a first output signal corresponding to a characteristic of the at least one component at the first monitoring location with a first optical computing device, the first optical computing device being arranged on a first movable housing that moves the first optical computing device along a first detection path, and the first optical computing device having a first integrated computational element (ICE) that optically interacts with the fluid along the first detection path and conveys optically interacted light to a first detector which generates the first output signal;
generating a second output signal corresponding to the characteristic at the second monitoring location with a second optical computing device, the second optical computing device being arranged on a second movable housing that moves the second optical computing device along a second detection path, and the second optical computing device having a second ICE that optically interacts with the fluid along the second detection path and conveys optically interacted light to a second detector which generates the second output signal;
receiving the first and second output signals with a signal processor; and
determining a difference between the first and second output signals with the signal processor,
wherein the characteristic of the at least one component is at least one of a Particle chord length, a particle chord length distribution, a particle morphology, a particle shape, a particle size, and a particle size distribution of the at least one component within the fluid.

17. The method of claim 16, wherein determining the difference between the first and second output signals further comprises determining how the characteristic of the at least one component changed between the first and second monitoring locations.

18. The method of claim 16, wherein the characteristic of the at least one component is a concentration of the at least one component in the fluid, the method further comprising:
determining the characteristic of the at least one component at the first monitoring location with the first optical computing device; and
determining the characteristic of the at least one component at the second monitoring location with the second optical computing device.

19. The method of claim 16, further comprising:
determining the characteristic of the at least one component at the first monitoring location with the first optical computing device; and
determining the characteristic of the at least one component at the second monitoring location with the second optical computing device.

* * * * *